(12) United States Patent
Kam (10) Patent No.: US 11,963,865 B2
(45) Date of Patent: Apr. 23, 2024

(54) ADJUSTABLE GRAFT PASSING/FIXATION LOOP

(71) Applicant: CONMED CORPORATION, Utica, NY (US)

(72) Inventor: Andrew Kam, Odessa, FL (US)

(73) Assignee: CONMED CORPORATION, Utica, NY (US)

( * ) Notice: Subject to any disclaimer, the term of this patent is extended or adjusted under 35 U.S.C. 154(b) by 838 days.

(21) Appl. No.: 16/447,580

(22) Filed: Jun. 20, 2019

(65) Prior Publication Data

US 2020/0188086 A1 Jun. 18, 2020

Related U.S. Application Data

(60) Provisional application No. 62/779,611, filed on Dec. 14, 2018.

(51) Int. Cl.
*A61F 2/08* (2006.01)
*A61B 17/04* (2006.01)
*A61F 2/46* (2006.01)

(52) U.S. Cl.
CPC .............. *A61F 2/0811* (2013.01); *A61F 2/46* (2013.01); *A61B 2017/0404* (2013.01); *A61B 2017/0459* (2013.01); *A61F 2002/0852* (2013.01)

(58) Field of Classification Search
CPC ........ A61F 2/0811; A61F 2/0805; A61F 2/46; A61F 2002/0847; A61F 2002/0852; A61B 17/0401; A61B 17/0469; A61B 17/0485; A61B 17/0487; A61B 17/06166; A61B 2017/0403; A61B 2017/0404; A61B 2017/0406; A61B 2017/0408; A61B 2017/0409; A61B 2017/0417; A61B 2017/0419; A61B 2017/0459; A61B 2017/0475; A61B 2017/0477; A61B 2017/0496; A61B 2017/06185
USPC ......................................................... 606/232
See application file for complete search history.

(56) References Cited

U.S. PATENT DOCUMENTS

| | | | |
|---|---|---|---|
| 6,533,802 B2 | 3/2003 | Bojarski et al. |
| 7,530,990 B2 | 5/2009 | Perriello et al. |
| 7,959,650 B2 | 6/2011 | Kaiser et al. |
| 8,118,836 B2 | 2/2012 | Denham et al. |
| 8,137,382 B2 | 3/2012 | Denham et al. |
| 8,231,654 B2 | 7/2012 | Kaiser et al. |
| 8,231,674 B2 | 7/2012 | Albertorio et al. |

(Continued)

*Primary Examiner* — Kankindi Rwego
(74) *Attorney, Agent, or Firm* — Bond, Schoeneck & King, PLLC; Frederick J. M. Price (57) ABSTRACT

A fixation device for graft placement and ligament suspension. The fixation device includes a strand of suture having a first limb and a second limb with a midpoint therebetween. The suture includes a first splice in the first limb and a second splice in the second limb. A first free end of the first limb extends through the second splice, forming a first loop with a diameter. A second free end of the second limb extends through the first splice, forming a second loop with a diameter. Tensioning the first free end reduces the diameter of the first loop and tensioning the second free end reduces the diameter of the second loop. The fixation device may include a button having the first and second limbs of suture woven therethrough such that the first and second free ends extend proximally from the button and the loops extend distally from the button.

19 Claims, 7 Drawing Sheets

(56) References Cited

U.S. PATENT DOCUMENTS

| | | | |
|---|---|---|---|
| 8,439,976 B2 | 5/2013 | Albertorio et al. | |
| 8,460,379 B2 | 6/2013 | Albertorio et al. | |
| 8,551,140 B2 | 10/2013 | Denham et al. | |
| 8,591,578 B2 | 11/2013 | Albertorio et al. | |
| 8,628,573 B2 | 1/2014 | Roller et al. | |
| 8,721,684 B2 | 5/2014 | Denham et al. | |
| 8,753,375 B2 | 6/2014 | Albertorio | |
| 8,771,316 B2 | 7/2014 | Denham et al. | |
| 8,784,426 B2 | 7/2014 | Smith et al. | |
| 8,840,645 B2 | 9/2014 | Denham et al. | |
| 8,882,833 B2 | 11/2014 | Saylor et al. | |
| 8,926,662 B2 | 1/2015 | Perriello et al. | |
| 9,005,245 B2 * | 4/2015 | Thornes | A61B 17/0401 606/232 |
| 9,101,461 B2 | 8/2015 | Albertorio et al. | |
| 9,149,267 B2 | 10/2015 | Norton et al. | |
| 9,179,950 B2 | 11/2015 | Zajac et al. | |
| 9,204,960 B2 | 12/2015 | Albertorio et al. | |
| 9,421,086 B2 | 8/2016 | Roller et al. | |
| 9,463,013 B2 | 10/2016 | Pilgeram et al. | |
| 9,498,204 B2 | 11/2016 | Denham et al. | |
| 9,510,821 B2 | 12/2016 | Denham et al. | |
| 9,572,655 B2 | 2/2017 | Denham et al. | |
| 9,642,610 B2 | 5/2017 | Albertorio et al. | |
| 9,687,338 B2 | 6/2017 | Albertorio et al. | |
| 9,782,161 B1 * | 10/2017 | Ferguson | A61B 17/04 |
| 9,801,708 B2 | 10/2017 | Denham et al. | |
| 10,004,489 B2 | 6/2018 | Kaiser et al. | |
| 10,004,493 B2 | 6/2018 | Stone et al. | |
| 10,022,118 B2 | 7/2018 | Norton et al. | |
| 10,064,716 B2 | 9/2018 | Norton | |
| 10,076,407 B2 | 9/2018 | Albertorio et al. | |
| 10,092,288 B2 | 10/2018 | Denham et al. | |
| 10,098,629 B2 | 10/2018 | Kaiser et al. | |
| 10,136,886 B2 | 11/2018 | Norton et al. | |
| 10,238,484 B2 | 3/2019 | Albertorio et al. | |
| 10,245,016 B2 | 4/2019 | Zajac et al. | |
| 10,285,801 B2 | 5/2019 | Roller et al. | |
| 10,383,617 B2 | 8/2019 | Rodriguez et al. | |
| 10,398,428 B2 | 9/2019 | Denham et al. | |
| 2004/0236373 A1 | 11/2004 | Anspach | |
| 2008/0287991 A1 | 11/2008 | Fromm | |
| 2008/0312689 A1 * | 12/2008 | Denham | A61F 2/0805 606/228 |
| 2011/0208239 A1 * | 8/2011 | Stone | A61B 17/06004 606/228 |
| 2012/0290002 A1 | 11/2012 | Astorino | |
| 2013/0317544 A1 * | 11/2013 | Ferguson | A61B 17/06166 606/228 |
| 2014/0074239 A1 * | 3/2014 | Albertorio | A61B 17/0401 606/232 |
| 2014/0081399 A1 * | 3/2014 | Roller | A61F 2/0811 606/232 |
| 2015/0057750 A1 | 2/2015 | Timmerman | |
| 2016/0151060 A1 * | 6/2016 | Albertorio | A61F 2/0811 606/232 |
| 2017/0128063 A1 | 5/2017 | Jackson | |
| 2017/0231752 A1 * | 8/2017 | Rodriguez | A61B 17/0401 623/13.14 |
| 2017/0273686 A1 | 9/2017 | Denham et al. | |
| 2017/0360425 A1 | 12/2017 | Stone et al. | |
| 2017/0360437 A1 * | 12/2017 | Ferguson | A61B 17/0401 |
| 2018/0000477 A1 | 1/2018 | Kaiser et al. | |
| 2018/0014864 A1 | 1/2018 | Stone et al. | |
| 2018/0042609 A1 | 2/2018 | Denham et al. | |
| 2018/0055507 A1 | 3/2018 | Bachmaier et al. | |
| 2018/0125476 A1 | 5/2018 | Kaiser et al. | |
| 2018/0125477 A1 | 5/2018 | Stone | |
| 2018/0153538 A1 | 6/2018 | Kaiser et al. | |
| 2018/0344447 A1 | 12/2018 | Albertorio et al. | |
| 2019/0038276 A1 | 2/2019 | Jackson | |
| 2019/0046185 A1 | 2/2019 | Norton et al. | |
| 2019/0125333 A1 | 5/2019 | Moore | |
| 2019/0321182 A1 * | 10/2019 | Spenciner | A61F 2/0811 |

* cited by examiner

ADJUSTABLE GRAFT PASSING/FIXATION LOOP

CROSS-REFERENCE TO RELATED APPLICATIONS

This application claims priority to U.S. Provisional Patent Application Ser. No. 62/779,611, filed on Dec. 14, 2018 and entitled "Adjustable Graft Passing/Fixation Loop," the entirety of which is incorporated herein by reference.

BACKGROUND OF THE INVENTION

1. Field of the Invention

The present invention is directed generally to a surgical system and, more particularly, to a fixation device for graft placement and ligament suspension.

2. Description of Related Art

The repair and reconstruction of torn or damaged soft tissues is a common surgical procedure. For example, replacement graft ligaments may be secured at the site of the original ligament. The procedure generally involves drilling bone tunnels into adjacent bones at the site of the original ligament and securing a graft ligament within these bone tunnels. In many applications, such as in the knee joint, such procedures may be performed arthroscopically. The graft ligament may be an autograft, an allograft, a xenograft, or it may be totally artificial and synthetic. Common types of anterior cruciate ligament (ACL) grafts, for example, include ones which may be autologous or allograft bone-patellar tendon-bone or soft tissue (such as semitendinosus and gracilis tendons), both types harvested by techniques well known to those skilled in the art.

The graft ligaments may be secured within the bone tunnels in a variety of ways. Of prime importance is the degree to which the graft ligaments can withstand pullout forces prior to complete healing. For example, it is known to use interference screws inserted parallel to the tunnel axis to compress the ends of the graft ligament against the wall of the bone tunnel to secure the graft ligament and promote tissue in-growth. However, interference screws are non-adjustable and may cause additional trauma to the surrounding tissue and bone.

Suspensory graft fixation devices have been developed to secure a graft ligament in a bone tunnel. One such device is described in U.S. Pat. No. 8,852,250 (Lombardo et al.), entitled Graft Fixation Implant, assigned to the assignee hereof and incorporated by reference in its entirety herein. Suspensory graft fixation devices work by lying transversely across the opening of a bone tunnel and generally take the form of an elongated anchor member which suspends a graft retaining loop from a fixation point on the surface of a bone to which the graft is to be attached (in this case, a femur). The elongated member has an axis and a pair of suture receiving apertures symmetrically situated on the axis on opposite sides of the center of the elongated member. In ACL procedures, the elongated member, often called a button, is adapted to be situated transversely across the exit opening of the bone tunnel on the lateral femoral cortex so that a supporting loop, generally made of suture material, can be suspended from the button and can extend into the bone tunnel from the suture receiving apertures of the button. The suture loop supports one end of a graft ligament passed through the loop. However, in many instances, the loops are not adjustable or cannot be adjusted after they are locked into place.

Therefore, there is a need for a fixation device for adjustably placing a graft and suspending a ligament that can be employed with or without a button.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention are directed to a fixation device for graft placement and ligament suspension. According to one aspect, the fixation device includes a strand of suture having a first limb and a second limb with a midpoint therebetween. The suture includes a first splice in the first limb and a second splice in the second limb. A first free end of the first limb extends through the second splice, forming a first loop with a diameter. A second free end of the second limb extends through the first splice, forming a second loop with a diameter. Tensioning the first free end reduces the diameter of the first loop and tensioning the second free end reduces the diameter of the second loop. The fixation device may also include a button having the first and second limbs of suture woven therethrough such that the first and second free ends extend proximally from the button and the loops extend distally from the button.

According to an alternative aspect, the present invention is a fixation device including a strand of suture having a first limb and a second limb with a midpoint therebetween. The suture includes a first splice in the first limb and a second splice in the second limb. A first free end of the first limb extends through the second splice, forming a first loop with a diameter. A second free end of the second limb extends through the first splice, forming a second loop with a diameter. The fixation device additionally includes a locking suture passing through the first splice and the second splice. Tensioning the first and second limbs does not collapse the first and second loops.

According to another aspect, the present invention is a method for suspending a tensioned object in a bone tunnel. The method includes the steps of: (i) providing a strand of suture having a first limb and a second limb with a midpoint therebetween; (ii) creating a first splice in the first limb and a second splice in the second limb; (iii) passing a first free end of the first limb through the second splice, forming a first loop with a diameter; and (iv) passing a second free end of the second limb through the first splice, forming a second loop with a diameter.

The method may additionally include the steps of: (v) tensioning the first free end of the first limb to reduce the diameter of the first loop; (vi) tensioning the second free end of the second limb to reduce the diameter of the second loop;

(vii) passing the first free end of the first limb through an object prior to passing the first free end through the second splice and passing the second free end of the second limb through an object prior to passing the second free end through the first splice; (viii) inserting the object into a bone tunnel; (ix) tensioning the first loop and the second loop by pulling the first free end and the second free end, respectively; and (x) locking the first loop and the second loop in place by passing a locking suture through the first splice and the second splice.

The term "suture" as used herein may be any type of filamentous material such as a biocompatible or bioabsorbable filament, ribbon, tape, woven or non-woven material capable of providing the loop support and the frictional resistance required by the device described herein.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
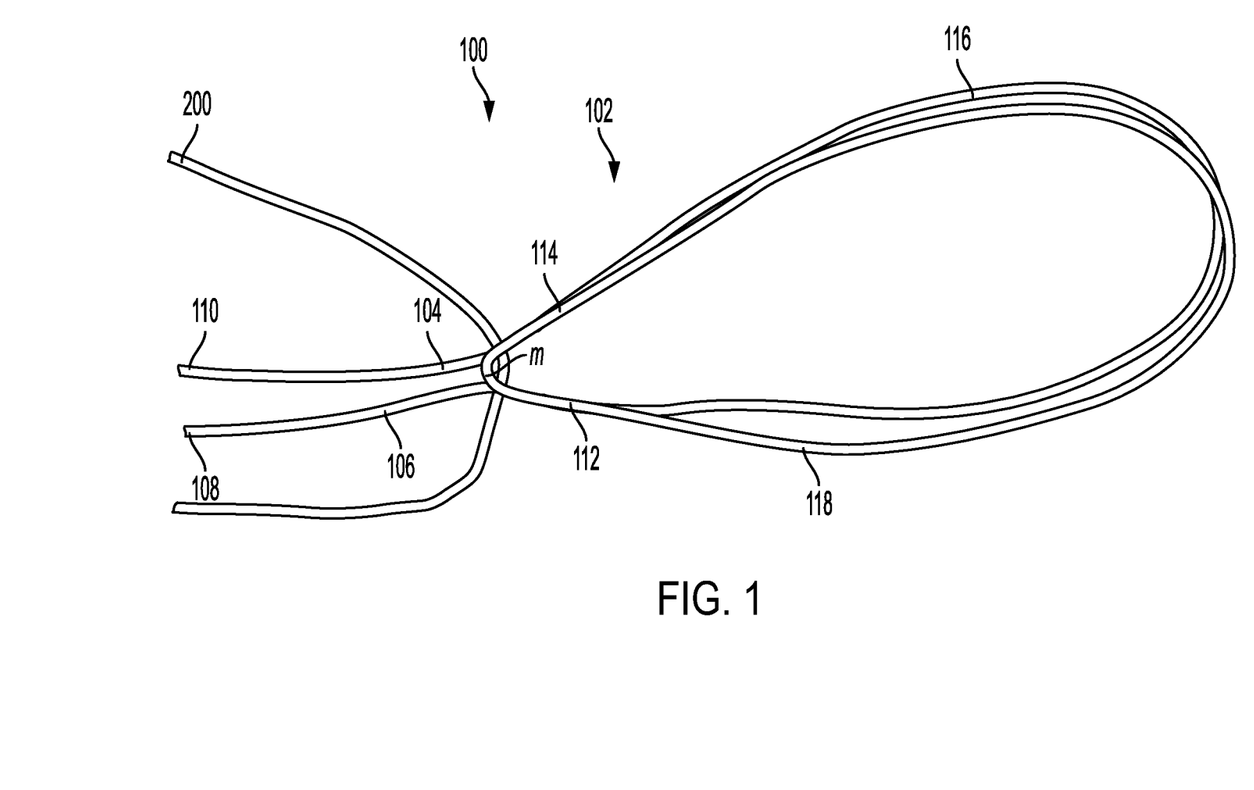
FIG. 1 is a perspective view schematic representation of a fixation device in the pre-deployment configuration, according to an embodiment.
Figure 2:
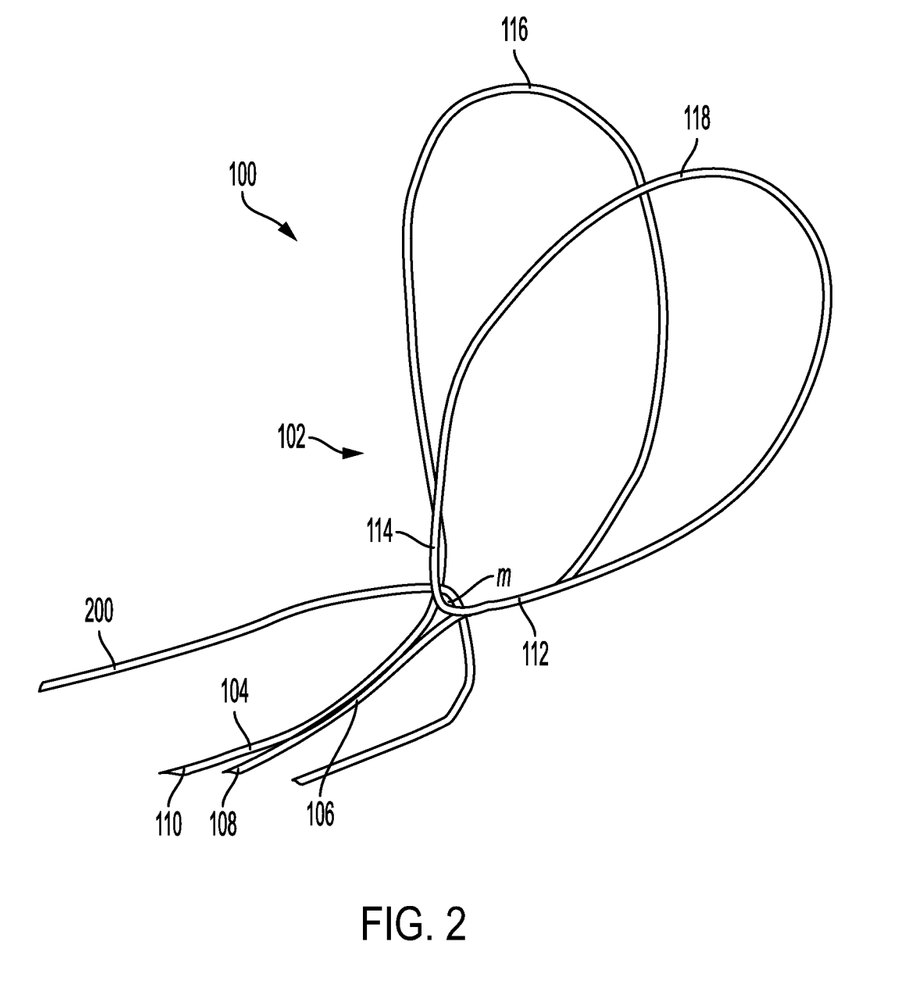
FIG. 2 is another perspective view schematic representation of the fixation device of FIG. 1.
Figure 3:
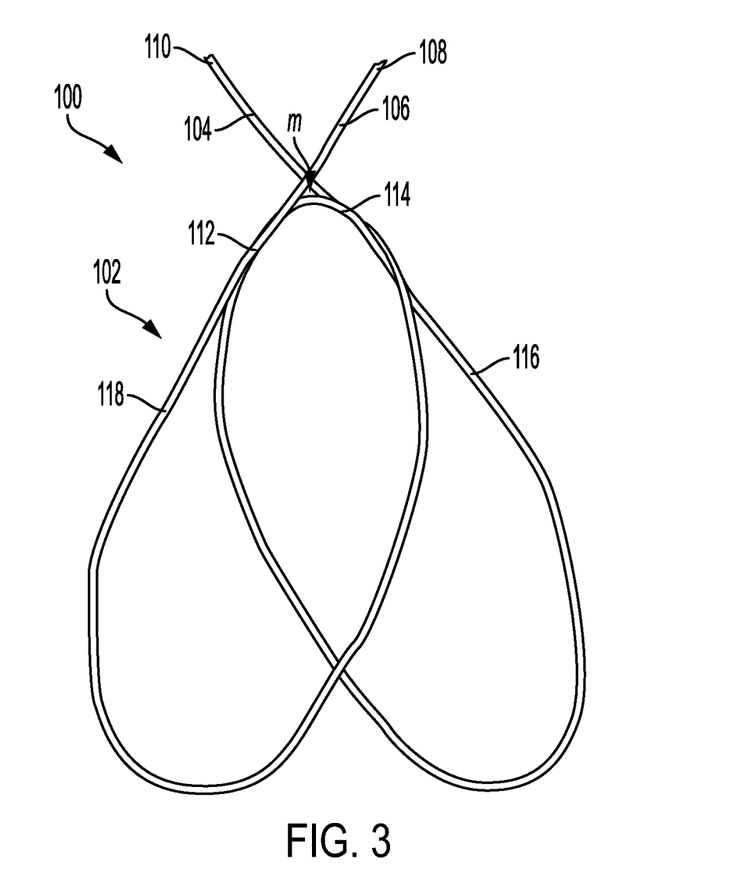
FIG. 3 is yet another perspective view schematic representation of a fixation device in the pre-deployment configuration, according to an embodiment.

Referring now to the figures, wherein like reference numerals refer to like parts throughout, FIGS. 1-3 show perspective views schematic representations of a fixation device 100, according to an embodiment. The fixation device 100 is comprised of a single strand of suture 102. The suture 102 is folded to create a first limb 104 and a second limb 106. In an embodiment, the suture 102 is folded in half such that the first limb 104 is substantially the same length as the second limb 106. The first limb 104 extends to a first free end 108 and the second limb 106 extends to a second free end 110.

Still referring to FIGS. 1-3, a first splice 112 is formed in the first limb 104 and a second splice 114 is formed in the second limb 106. To achieve a pre-deployment configuration shown in FIG. 1, the first free end 108 is passed through the second splice 114 and the second free end 110 is passed through the first splice 112. In the pre-deployment configuration, there is a midpoint in between the first splice 112 and the second splice 114. In an embodiment, the first free end 108 exits the second splice 114 approximately at the midpoint m and the second free end 110 exits the first splice 112 approximately at the midpoint m.

As shown in FIGS. 1-3, passing the free ends 108, 110 of the suture 102 through the splices 112, 114 forms a first loop 116 and a second loop 118 in the suture 102. The first loop 116 is formed in the first limb 104 and the second loop 118 is formed in the second limb 106. In the pre-deployment configuration shown in FIGS. 1-3, the loops 116, 118 extend distally from the splices 112, 114. The first loop 116 is independent from the second loop 118 such that the loops 116, 118 are not interconnected.

In order to load a graft (not shown) onto the fixation device 100, the free ends 108, 110 of the suture 102 are passed through the graft prior to passing through the splices 112, 114. The first limb 104 is passed through the graft prior to passing through the second splice 114 and the second limb 106 is passed through the graft prior to the passing through the first splice 112. As a result, the first limb 104 and the second limb 106 both pass through the graft such that the graft is attached to both the first and second loops 116, 118.

Figure 4:
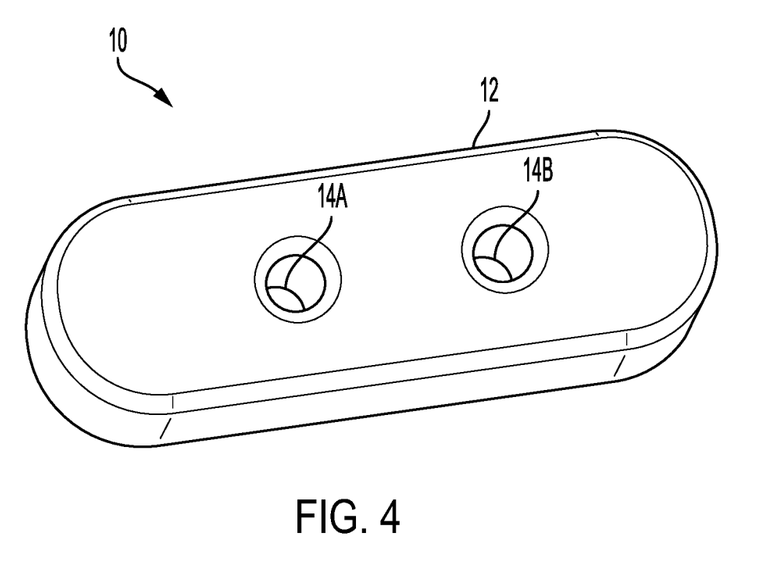
FIG. 4 is a perspective view schematic representation of a button, according to an exemplary embodiment.

In an alternative embodiment, a button 10, such as that shown in FIG. 4, can be used in conjunction with the loops 116, 118 to suspend a graft over a bone tunnel. The button 10 can be an elongated member 12 with at least two spaced apertures 14A, 14B. When using the button 10, the suture 102 is inserted into the button 10 such that the first limb 104 extends through a first aperture 14A and the second limb 106 extends through a second aperture 14B. The free ends 108, 110 of the suture 102 are threaded through the splices 112, 114 as described above.

Thereafter, the first free end 108 of the suture 102 can be passed through the second aperture 14B in the proximal direction and the second free end 110 of the suture 102 is passed through the first aperture 14A in the proximal direction such that the free ends 108, 110 of the suture 102 extend proximally from the button 10, while the loops 116, 118, extend distally from the button 10. Any known surgical button or other suspensory graft fixation device can be used. An exemplary suspensory graft fixation device is shown and described in U.S. Pat. No. 9,931,197 issued on Apr. 3, 2018, and incorporated herein by reference in its entirety.

Figure 5:
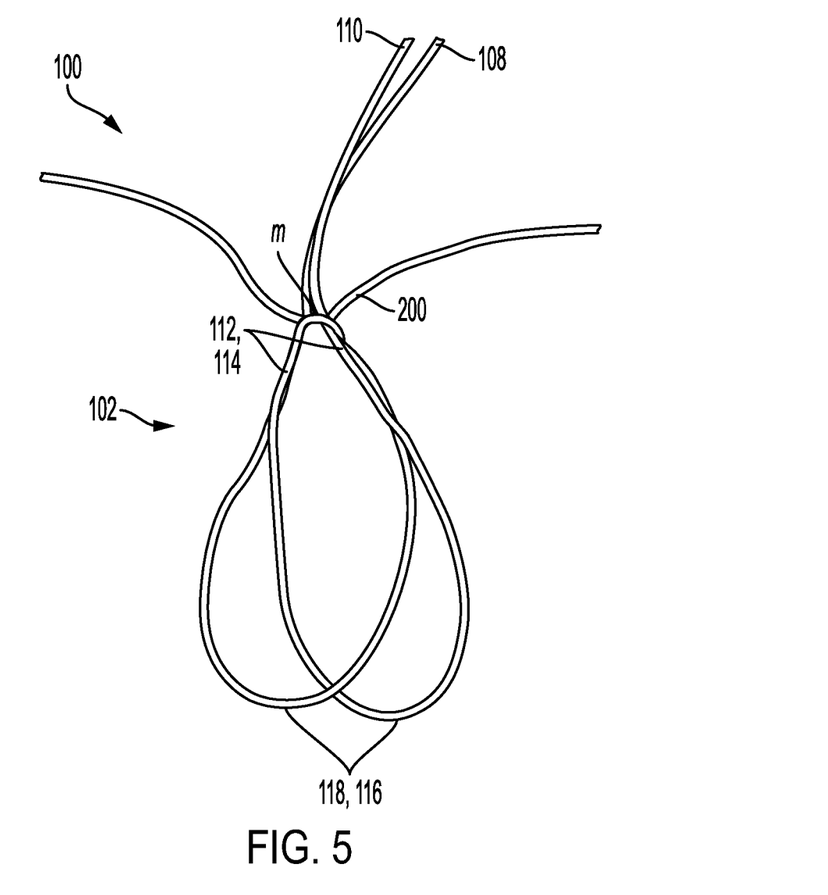
FIG. 5 is a perspective view schematic representation of a fixation device in the pre-deployment configuration, according to an alternative embodiment.

Referring now to FIG. 5, there is shown a perspective view schematic representation of the fixation device 100, according to an embodiment. In the depicted embodiment, a locking suture 200 is transversely woven through the first splice 112 and the second splice 114 of the device 100 in the pre-deployment configuration. When the locking suture 200 is woven through both splices 112, 114, the first free end 108 of the suture 102 and the second free end 110 of the suture 102 cannot move independently. As a result, the first and second loops 116, 118 are locked such that the size (i.e., diameter) of the loops 116, 118 cannot be adjusted when the locking suture 200 is in place as shown.

The fixation device 100 described above can be used to fixate a graft in a bone tunnel or against a surface of a bone and suspend a ligament in a desired relative position to a bone (as should be understood by a person of ordinary skill in the art in conjunction with a review of this disclosure). For graft fixation uses, the graft can be attached to the loops 116, 118 as described above. For example, the limbs 104, 106 of the device 100 are passed through the graft prior establishing the pre-deployment configuration shown in FIGS. 1-3. For certain ligament suspension uses, the limbs 104, 106 can be similarly passed through or around the ligament prior to establishing the pre-deployment configuration shown in FIGS. 1-3.

With the graft attached to the loops 116, 118, the graft can be inserted into a bone tunnel. When the loops 116, 118 are locked, the fixation device 100 allows for the passing of the graft through the bone tunnel. Having the loop 116, 118 locked allows the surgeon to pass the free ends 108, 110 of the suture 102 through the bone tunnel and subsequently pull on the free ends 108, 110 to dock the graft into the bone socket, without collapsing the loops 116, 118. Thereafter, the loops 116, 118 can be subsequently adjusted to sufficiently tension the graft.

Similarly, for ligament suspension, the loops 116, 118 can be used to pull and suspend the ligament in a desired, relative position to a bone. The tension on the loops 116, 118 can be adjusted using the free ends 108, 110 of the suture 102. Pulling the first free end 108 of the suture 102 reduces the size of the first loop 116 from a first diameter to a smaller, second diameter. Likewise, pulling the second free end 110 of the suture 102 reduces the size of the second loop 118 from a first diameter to a smaller, second diameter.

If less tension is desired in the first and second loops 116, 118, tractioning or pulling at the midpoint m allows the first limb 104 to slide within the second splice 114, expanding the first diameter of the first loop 116 to a larger, second diameter. Similarly, tractioning or pulling at the midpoint 711 allows the second limb 106 to slide within the first splice 112, expanding the first diameter of the second loop 118 to a larger, second diameter. When the loops 116, 118 have been sufficiently tensioned, the locking suture 200 can be passed through the splices 112, 114. With the locking suture 200 passed through the splices 112, 114, the size of the loops 116, 118 cannot be adjusted.

In an embodiment where the device 100 includes a button 10 (FIG. 4) the button 10 can be used to maintain the achieved tension in the loops 116, 118. The button 10 can be secured across the bone hole at the entrance of the bone tunnel. The free ends 108, 110 of the limbs 104, 106 can be knotted or otherwise locked to secure the button 10 in place.

Figure 6:
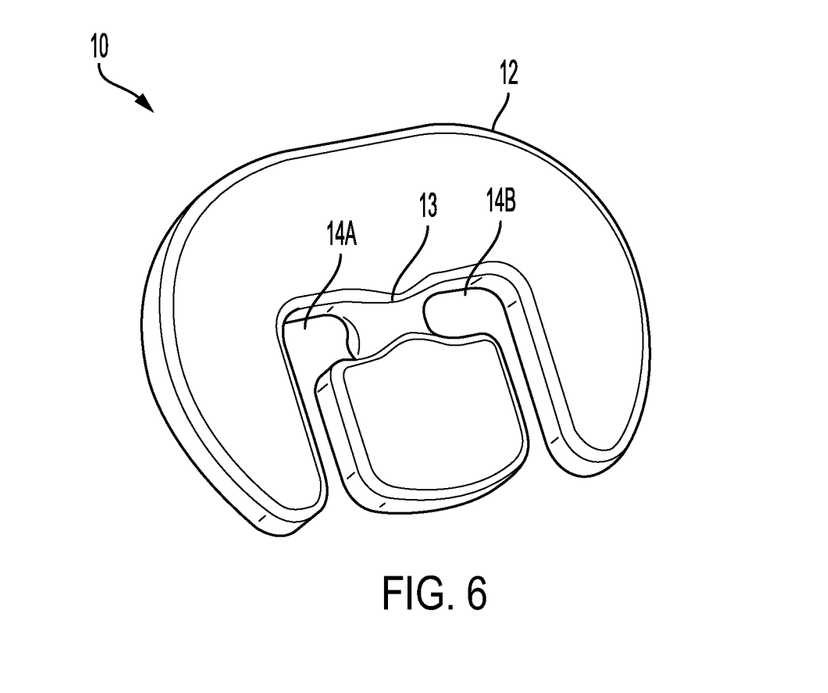
FIG. 6 is a perspective view schematic representation of a button, according to an alternative exemplary embodiment.
Figure 7:
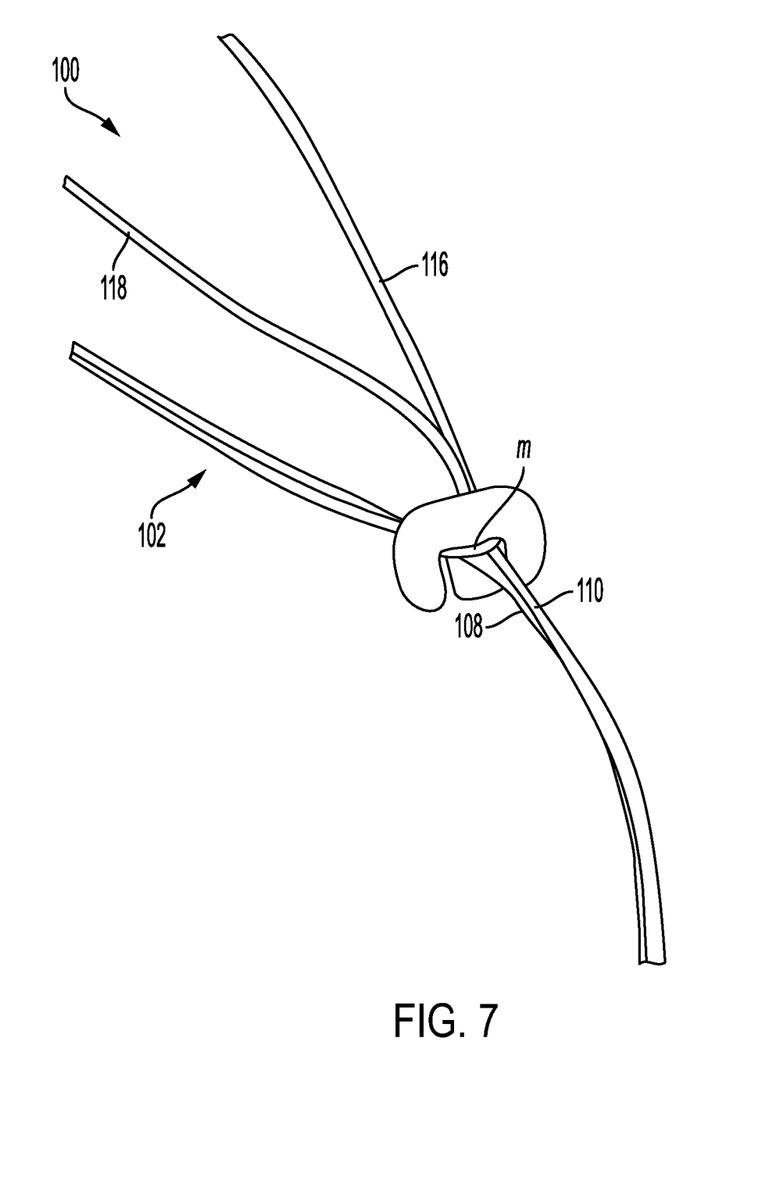
FIG. 7 is a perspective view schematic representation of a fixation device, with the button of FIG. 6, in the pre-deployment configuration, according to yet another embodiment.

In another embodiment, an alternative button 10 shown in FIG. 6 is used to suspend the first and second loops 116, 118 within a bone hole. The embodiment of the button 10 shown in FIG. 6 comprises an elongated member 12 including two spaced slots 14A, 14B (instead of two spaced apertures) with a bridge 13 therebetween. When using the button 10 shown in FIG. 6, the button 10 is loaded onto the suture 102. Specifically, as shown in FIG. 7, the button 10 slides through the midpoint m in the suture 102. The portion of the suture 102 at the midpoint m is wrapped around the bridge 13 such that the first and second loops 116, 118 extend distally from the slots 14A, 14B. The free ends 108, 110 of the suture 102 extend proximally from the slots 14A, 14B. The free ends 108, 110 of the suture 102 are used, in the methods described above, to reduce the first and second loops 116, 118, bringing the button 10 against a bone hole of a bone tunnel.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A fixation device, comprising:
a strand of suture comprising a first limb and a second limb with a midpoint therebetween;
a first splice positioned in the first limb and a second splice positioned in the second limb, wherein the first splice has a first splice entrance and a first splice exit and the second splice has a second splice entrance and a second splice exit, wherein the first splice entrance and first splice exit are different from the second splice entrance and the second splice exit, respectively;
a first free end of the first limb extending through the second splice, forming a first loop with a diameter;
a second free end of the second limb extending through the first splice, forming a second loop with a diameter;
wherein each of the first free end and the second free end extends away from each of the first loop and the second loop; and
wherein tensioning the first free end in a first direction away from the midpoint reduces the diameter of the first loop and tensioning the second free end in a second direction away from the midpoint reduces the diameter of the second loop; and
a locking suture passing through the first splice and the second splice.

2. The device of claim 1, further comprising a button having the first and second limbs of the strand of suture woven therethrough.

3. The device of claim 2, wherein the first and second free ends extend proximally from the button and the first and second loops extend distally from the button.

4. The device of claim 2, further comprising a first aperture and an adjacent, second aperture positioned through the button.

5. The device of claim 4, wherein the first limb extends distally through the first aperture and the second limb extends distally through the second aperture.

6. The device of claim 5, wherein the second free end extends proximally through the first aperture and the first free end extends proximally through the second aperture.

7. The device of claim 1, wherein the strand of suture is composed of at least one of the following: biocompatible filament, bioabsorbable filament, ribbon, tape, woven material, and non-woven material.

8. The device of claim 1, wherein the diameter of the second loop can be increased by pulling on the second limb at the midpoint in a direction opposite the second direction.

9. The fixation device of claim 1, wherein the midpoint is positioned between the first splice and the second splice.

10. A method for suspending a tensioned object in a bone tunnel, comprising the steps of:
providing a strand of suture having a first limb and a second limb with a midpoint therebetween;
creating a first splice in the first limb and a second splice in the second limb;
wherein the first splice has a first splice entrance and a first splice exit and the second splice has a second splice entrance and a second splice exit, wherein the first splice entrance and first splice exit are different from the second splice entrance and the second splice exit, respectively;
passing a first free end of the first limb through the second splice in a first direction, forming a first loop with a diameter;
passing a second free end of the second limb through the first splice, forming a second loop with a diameter;
wherein each of the first free end and the second free end extends away from each of the first loop and the second loop;
passing the first free end of the first limb through an object prior to the step of passing the first free end through the second splice; and
passing the second free end of the second limb through the object prior to the step of passing the second free end through the first splice.

11. The method of claim 10, further comprising the step of tensioning the first free end of the first limb in the first direction away from the midpoint to reduce the diameter of the first loop.

12. The method of claim 10, further comprising the step of tensioning the second free end of the second limb in the second direction away from the midpoint to reduce the diameter of the second loop.

13. The method of claim 10, further comprising the step of inserting the object into a bone tunnel.

14. The method of claim 13, further comprising the step of tensioning the first loop and the second loop by pulling the first free end and the second free end, respectively.

15. The method of claim 14, further comprising the step of locking the first loop and the second loop in place by passing a locking suture through the first splice and the second splice.

16. The method of claim 10, further comprising the steps of:
providing an elongated member having a first aperture and an adjacent, second aperture; and
passing the first limb through the first aperture and the second limb through the second aperture.

17. The method of claim 16, further comprising the steps of:
passing the first free end proximally through the second aperture after passing the first free end through the first splice; and
passing the second free end proximally through the first aperture after passing the second free end through the second splice.

18. The method of claim 10, wherein the midpoint is positioned between the first splice and the second splice.

19. A fixation device, comprising:
a strand of suture comprising a first limb and a second limb with a midpoint therebetween;
a first splice positioned in the first limb and a second splice positioned in the second limb;
a first free end of the first limb extending through the second splice, forming a first loop with a diameter;
a second free end of the second limb extending through the first splice, forming a second loop with a diameter;
a locking suture passing through the first splice and the second splice; and
wherein tensioning the first and second limbs does not collapse the first and second loops.

* * * * *